(12) United States Patent
Nilson et al.

(10) Patent No.: US 9,463,303 B2
(45) Date of Patent: *Oct. 11, 2016

(54) SECUREMENT DEVICE FOR MEDICAL FIXTURES

(71) Applicant: SecurCath LLC, North Barrington, IL (US)

(72) Inventors: Torsten Nilson, North Barrington, IL (US); Jacques A. LaRose, Round Lake, IL (US)

(73) Assignee: IP PrimeGuard Medical, LLC, North Barrington, IL (US)

( * ) Notice: Subject to any disclaimer, the term of this patent is extended or adjusted under 35 U.S.C. 154(b) by 420 days.

This patent is subject to a terminal disclaimer.

(21) Appl. No.: 14/052,139

(22) Filed: Oct. 11, 2013

(65) Prior Publication Data

US 2014/0039402 A1     Feb. 6, 2014

Related U.S. Application Data

(63) Continuation of application No. 13/333,091, filed on Dec. 21, 2011, now Pat. No. 8,556,859.

(51) Int. Cl.
*A61M 25/02*     (2006.01)

(52) U.S. Cl.
CPC ........ *A61M 25/02* (2013.01); *A61M 2025/024* (2013.01); *A61M 2025/0266* (2013.01)

(58) Field of Classification Search
CPC ......... A61M 25/02; A61M 2025/024; A61M 2025/0266; A61M 2025/0246; A61M 2025/028; A61M 2025/0253
See application file for complete search history.

(56) References Cited

U.S. PATENT DOCUMENTS

| 6,283,945 B1 | 9/2001 | Bierman | |
| 8,556,859 B2 * | 10/2013 | Nilson | A61M 25/02 604/174 |
| 8,827,959 B2 * | 9/2014 | Wright | A61M 25/02 604/174 |
| 2007/0142784 A1 | 6/2007 | Dikeman et al. | |
| 2010/0114034 A1 | 5/2010 | Wright et al. | |

FOREIGN PATENT DOCUMENTS

| WO | 2010090908 A2 | 8/2010 |
| WO | 2011060197 A1 | 5/2011 |

OTHER PUBLICATIONS

Notification Concerning Transmittal of International Preliminary Report on Patentability (Chapter I of the Patent Cooperation Treaty) dated Jul. 3, 2014; International Application No. PCT/US2012/069649; International Filing Date: Dec. 14, 2012; Applicant: Securcath LLC.

* cited by examiner

*Primary Examiner* — Aarti B Berdichevsky
(74) *Attorney, Agent, or Firm* — Erise IP, P.A.

(57) ABSTRACT

A securement device for retaining medical tubing, catheters, and other medical fixtures proximal a patient's skin. The device has a base, at least one channel formed in the base, a flexible strap for overlying the base, and a coupling assembly for coupling the strap to the base. Embodiments for use with Foley catheters include a plurality of channels of differing diameters. Embodiments for use with a peripheral catheter include a single channel for retaining a spin nut. The coupling assembly includes left and right tracks in left and right sides of the base, and left and right rails on an underside of the flexible strap at left and right ends of a body of the strap. The left rail is removably coupled and held within the left track on the base, and the right rail is removably coupled and held within the right track on the base.

20 Claims, 11 Drawing Sheets

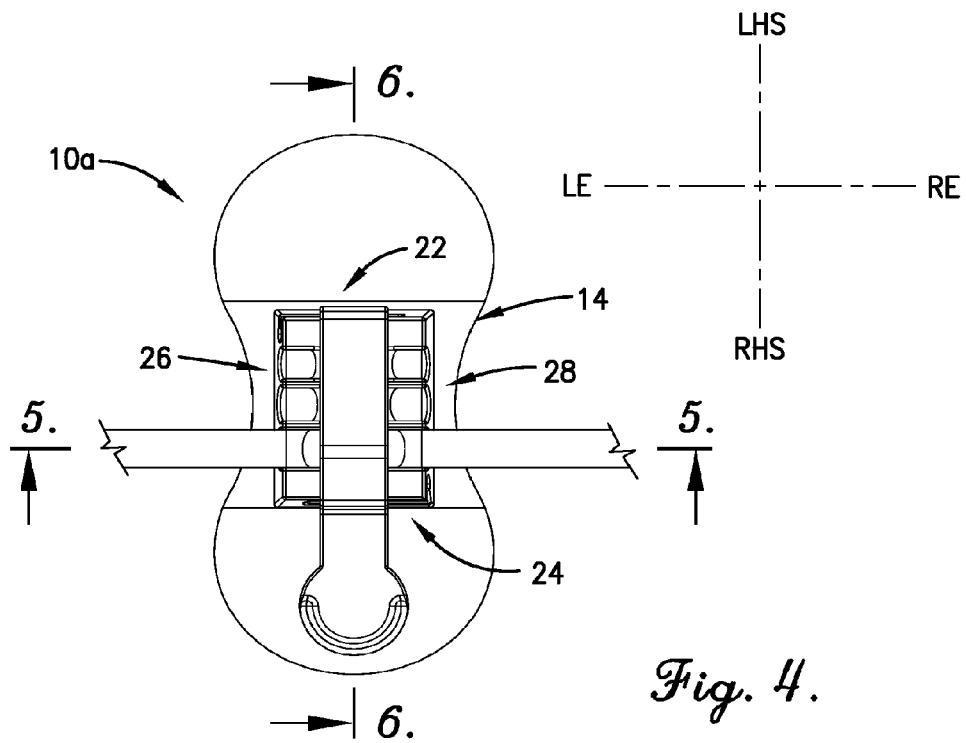
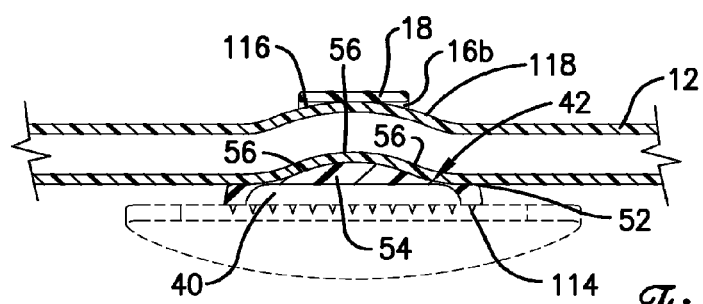
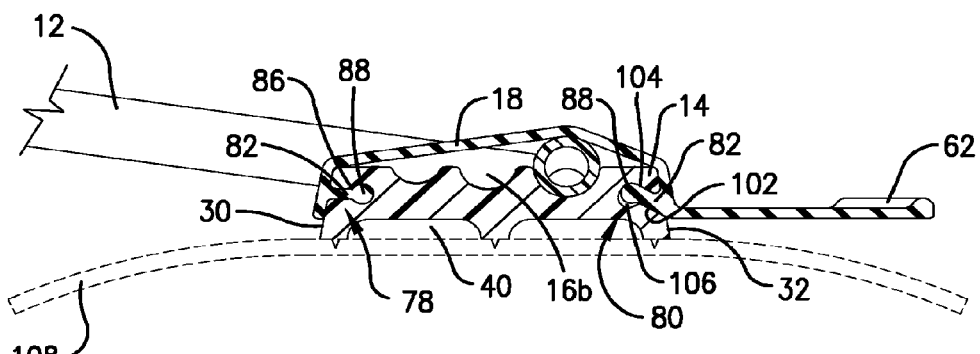

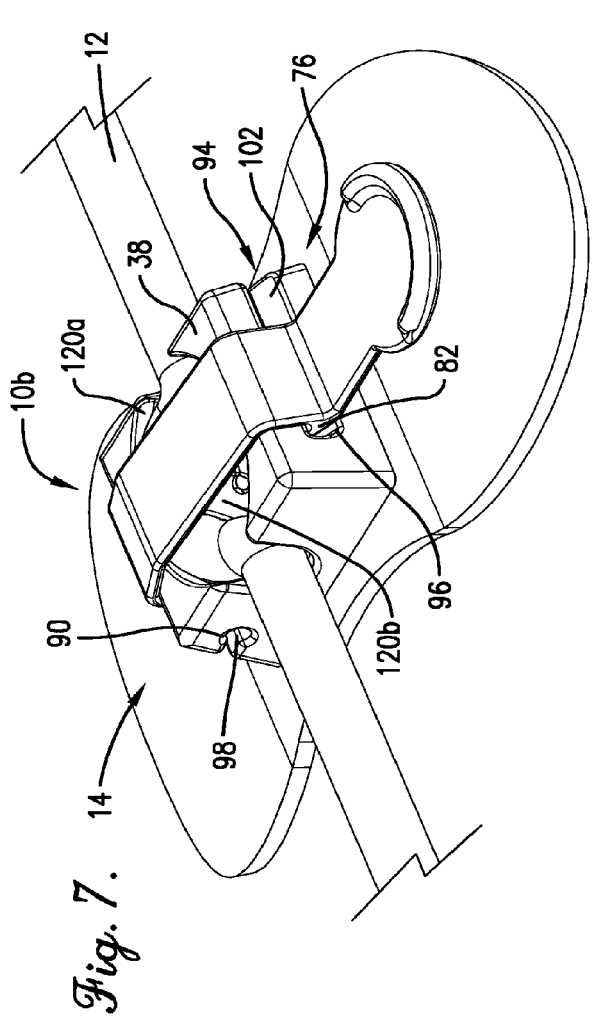
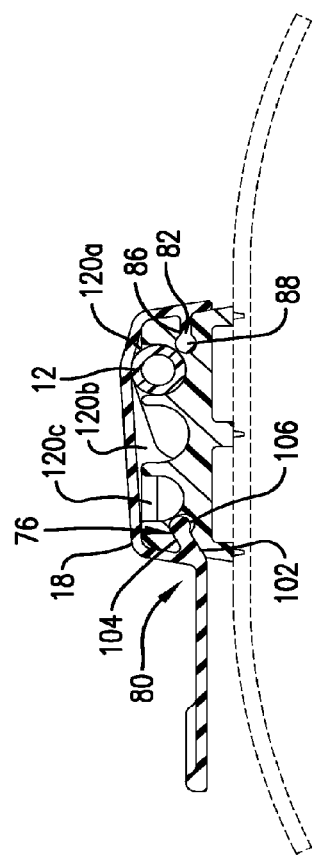
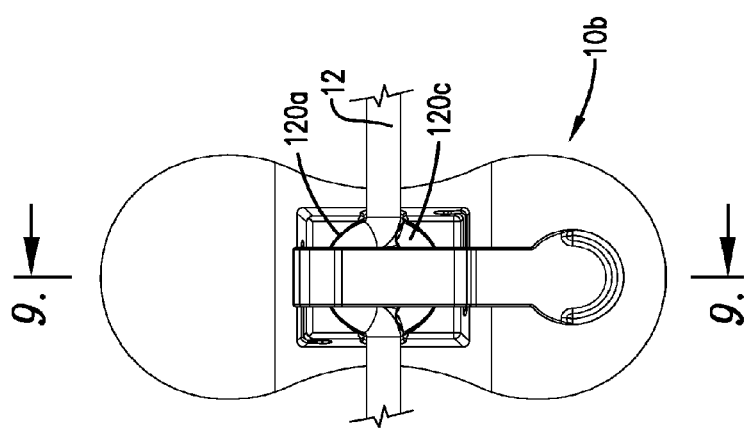

SECUREMENT DEVICE FOR MEDICAL FIXTURES

RELATED APPLICATION

This application is a continuation patent application and claims priority benefit, with regard to all common subject matter, of earlier-filed U.S. patent application Ser. No. 13/333,091, entitled "SECUREMENT DEVICE FOR MEDICAL FIXTURES," filed Dec. 21, 2011, now U.S. Pat. No. 8,556,859, issued Oct. 15, 2013. The above-referenced patent is hereby incorporated by reference into the present application in its entirety.

BACKGROUND

1. Field

Embodiments of the present invention are securement devices for securing medical lines, tubing, and other fixtures proximal a patient's skin to restrict movement of the medical line, tubing, or fixture.

2. Related Art

Securement devices are commonly used for retaining indwelling catheters and, more particularly, for restricting movement of the catheter relative to the patient's skin. When a patient has a catheter percutaneously inserted, the medical fixtures accompanying the catheter, such as tubing, luers, catheter adaptors, and catheter hubs, are located proximal to the catheter insertion site. Movement of the medical fixtures may result in very slight movement of the catheter or medical tubing into and out of the patient's skin. This slight movement of the catheter risks introduction of microbes into the patient's bloodstream, which is a leading cause of bloodstream infections. Even in instances where bloodstream infection or other blood-related adverse effects, such as thrombosis, are not of concern, it is still desirable to secure the medical fixtures against the patient's skin to prevent dislodgement of or interference with the indwelling catheter.

Although mechanical securement devices beyond suturing and tape are known, such securement devices often require good hand dexterity, can be cumbersome to use and bulky, and, most notably, do not inhibit substantially all movement of the catheter. Accordingly, there is a need for a securement device that addresses the above problems and provides an easily manipulateable device that substantially completely inhibits movement of the indwelling catheter relative to the patient's skin. Additionally, for certain types of catheters, such as Foley catheters, the catheters come in different sizes. In an effort to restrict movement of the catheter, the mechanical securement device often is only configured for use with one type or size of catheter. Accordingly, there is a need for a securement device that can be used with more than one catheter size.

SUMMARY OF THE INVENTION

Embodiments of the present invention solve the above-mentioned problems and provide a distinct advance in the art of securement devices for medical fixtures. More particularly, embodiments of the present invention provide a securement device that restricts or otherwise inhibits movement of an indwelling catheter relative to the patient's skin.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

In a first embodiment of the present invention, a securement device for use with a Foley catheter is provided, wherein the securement device may be used with a plurality of differently-sized medical tubing associated with the Foley catheter. Alternatively, the securement device of the first embodiment may be used with other medical fixtures, such as medical tubing. The securement device broadly comprises a base and at least two and, in embodiments of the present invention, three generally straight, parallel channels each formed in the base. Each channel has a different diameter for retaining a medical tubing of different sizes. The securement device of the first embodiment also includes a flexible strap for securing the medical tubing in the channel during use of the securement device and a coupling assembly for removably coupling the flexible strap to the base.

A second embodiment of the present invention is a securement device also for use with a Foley catheter. Alternatively, the securement device of the second embodiment may be used with other medical fixtures, such as medical tubing. Unlike the first embodiment comprising three straight, parallel channels, the securement device of the second embodiment comprises three channels arranged side-by-side that intersect along a portion of their respective lengths. The two outer channels are inwardly curved towards the middle channel, such that a portion of the longitudinal length of each of the channels intersects. A flexible strap and coupling assembly retain the medical tubing within the channel of the device.

A third embodiment of the present invention is a securement device for use with peripheral catheters, such as a peripherally inserted central catheter ("PICC"), a peripherally inserted venous catheter ("PIVC"), or a central venous catheter ("CVC"). More particularly, the securement device retains a spin nut conventionally coupled with a catheter hub of a peripheral catheter. A channel is formed in the base, and the spin nut is retained in the channel. The base has front and rear end walls (although the end wall may be optional) that each include a generally semi-circular cut-out having a diameter or width less than a diameter or width of the channel. Thus, interior faces of the front and rear end walls and the channel together form a receiving area for a generally bottom half of the spin nut. In use, a front face of the spin nut contacts the interior face of the front end wall, and similarly, a rear face of the spin nut contacts the interior face of the rear end wall. As with the first and second embodiments, the spin nut is also retained within the catheter via use of a flexible strap and coupling assembly.

The coupling assembly for each of the embodiments broadly comprises left and right tracks formed in left and right side walls of the base, and left and right rails formed on an underside of the flexible strap at generally left and right ends of a body of the strap. The left rail on the strap is removably coupled and held within the left track on the base, and the right rail on the strap is removably coupled and held within the right track on the base.

BRIEF DESCRIPTION OF THE DRAWING FIGURES

Embodiments of the present invention are described in detail below with reference to the attached drawing figures, wherein:

FIG. 4 is a plan view of the securement device of FIG. 2 and further illustrating a set of orientation axes;

FIG. 5 is a vertical cross-sectional view through line 5-5 of FIG. 4 and particularly illustrating a concavity in a channel(s) of the securement device;

FIG. 6 is a vertical cross-sectional view through line 6-6 of FIG. 4 and particularly illustrating a coupling assembly of the securement device;

FIG. 7 is a front isometric view of a securement device of a second embodiment of the present invention for use with a Foley catheter and particularly illustrating the medical fixture comprising medical tubing retained within a leftmost channel of the device;

FIG. 8 is a plan view of the securement device of FIG. 7;

FIG. 9 is a vertical cross-sectional view through line 9-9 of FIG. 8 and particularly illustrating the coupling assembly of the securement device;

Figure 1:
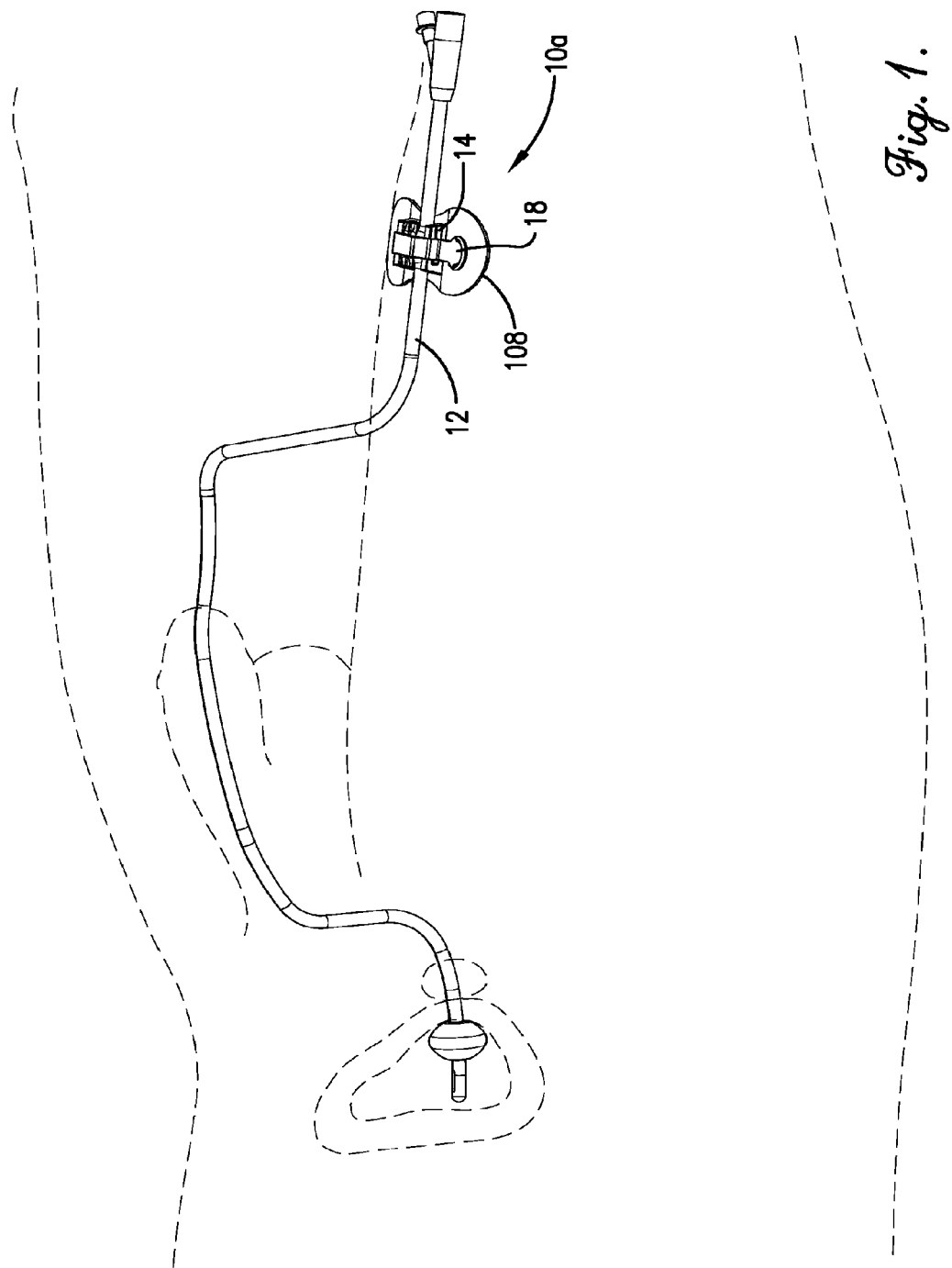
FIG. 1 is an environmental view of a securement device of a first embodiment of the present invention for use with a Foley catheter, wherein the securement device is secured in a patient's groin area.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Embodiments of the present invention are securement devices for medical fixtures and methods of using the securement devices to secure the medical fixtures to a skin of a patient. As used herein, "medical fixture" comprises medical tubing, a medical line, a medical adaptor, a medical fitting, or any other type of medical fixture used, either singly or with other medical devices, to withdraw or insert fluids into a patient. Exemplary and non-limiting medical fixtures include the medical tubing of a Foley catheter, the spin nut of a peripheral catheter, or a luer connector.

Three different embodiments of securement devices will be described herein. The embodiments have certain structural features that are the same in each of the embodiments, and similar structural features will be annotated with like reference numerals. It is to be understood that the structural features of the embodiments can be interchanged, such that the presentation of the three embodiments in the present description is not intended to be limiting on the variances or permutations of securement devices having the features described herein.

First Embodiment of a Securement Device for a Foley Catheter

Referring now to the embodiment disclosed in FIGS. 1-6, a securement device 10a for a medical fixture 12 comprising a Foley catheter is illustrated. The securement device 10a broadly comprises a base 14, a plurality of channels 16a-c formed in the base 14, a flexible strap 18, and a coupling assembly 20 for removably coupling the strap 18 to the base 14. Referring to the plan view of FIG. 4 and the provided orientation axes, features of the securement device 10a will be described with reference to a left side 22 (marked as LHS (left hand side) on the orientation axes), a right side 24 (RHS), a front end 26 (FE), and a rear end 28 (RE). A width of the base 14 is measured from the left side 22 to the right side 24, and a length of the base 14 is measured from the front end 26 to the rear end 28. The axis from the left side 22 to the right side 24 of the base is a lateral or transverse axis, and the axis from the front end 26 to the right end 28 of the base is a longitudinal axis.

Figure 2:
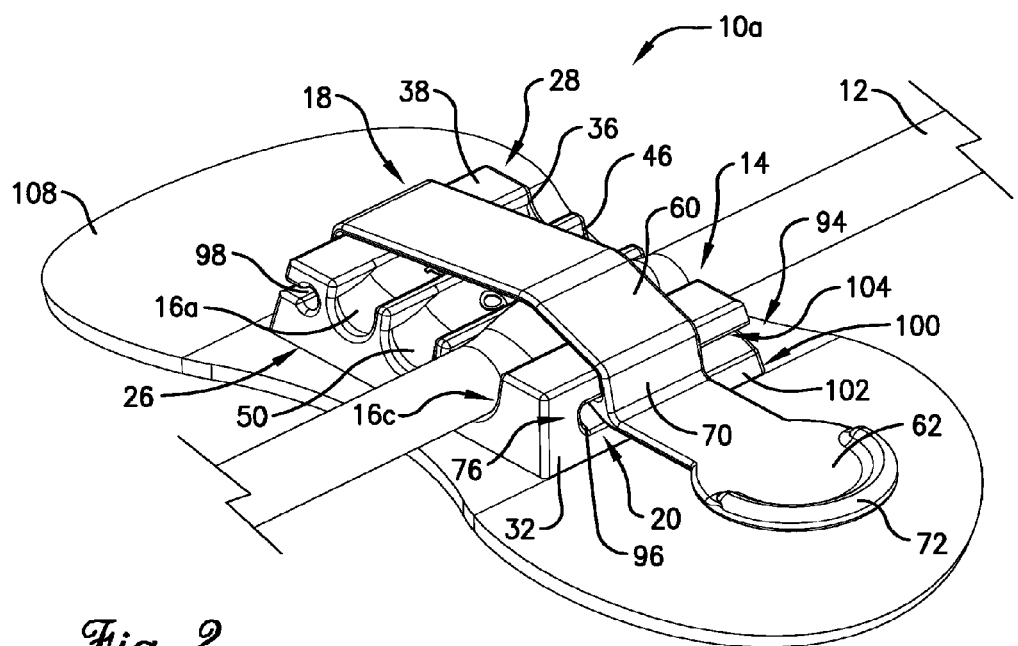
FIG. 2 is a front isometric view of the securement device of the first embodiment and illustrating a medical fixture comprising medical tubing retained in a channel of the device.
Figure 3:
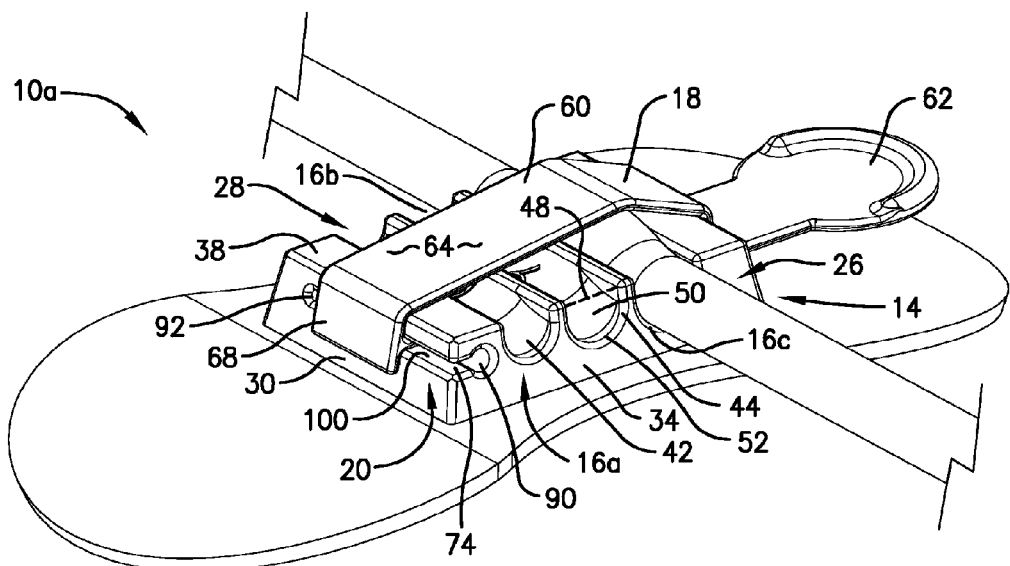
FIG. 3 is another front isometric view of the securement device of FIG. 2.
Figure 10:
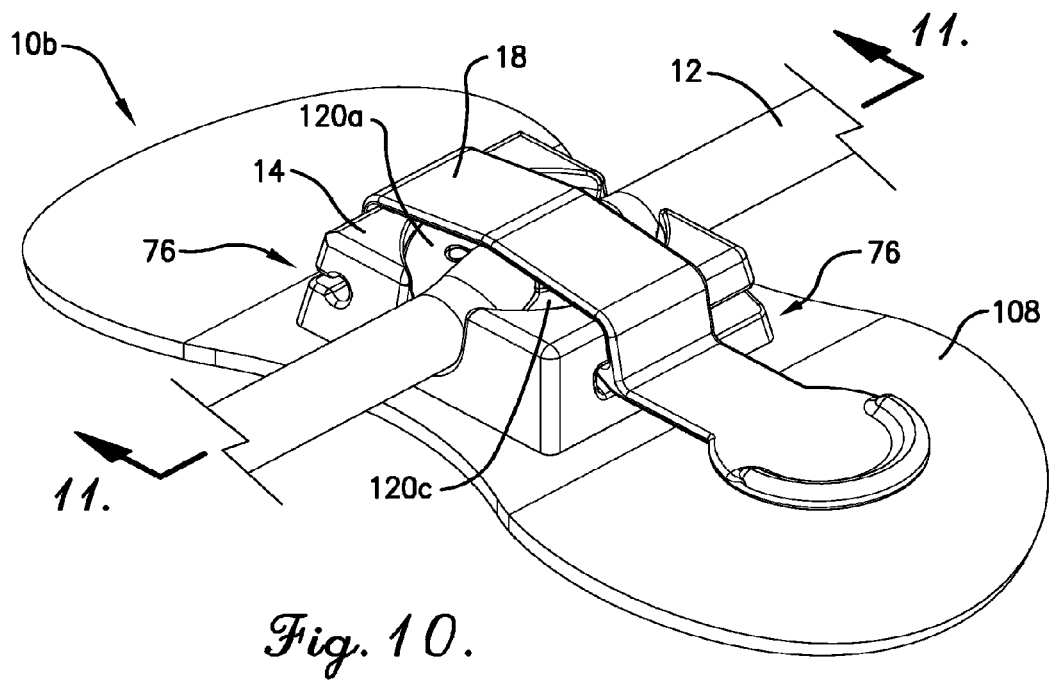
FIG. 10 is a front isometric view of the securement device of FIG. 7 and particularly illustrating the medical tubing retained in a middle channel of the device.

As illustrated in FIGS. 2-3 and 6, the base 14 includes a left side wall 30 on the left side 22 of the base, a right side wall 32 on the right side 24 of the base, a front end wall 34 on the front end 26 of the base, a rear end wall 36 on the rear end 28 of the base, a top wall 38, and a bottom wall 40. The base 14 is formed of a substantially rigid material, and in embodiments of the present invention, is formed of ABS or other plastic or suitable material that is accepted for medical use as a USP Class VI material or otherwise approved by the FDA. In embodiments of the present invention, the base 14 may include a bacterial or microbial inhibitor either coated on the base or manufactured into the base 14 material. The width of the base 14 is approximately 10-50 mm, approximately 20-40 mm, or approximately 25-35 mm. The length of the base 14 is approximately 5-35 mm, approximately 10-30 mm, or approximately 15-25 mm. A height of the base 14 from the bottom wall 40 to the top wall 38 is approximately 2-15 mm, approximately 5-12 mm, or approximately 6-10 mm.

As illustrated in the embodiment of FIGS. 1-6, three channels 16a, 16b, and 16c are formed side-by-side in the top wall 38 of the base 14 to accommodate medical tubing 12 of different diameters. As noted above, the securement device 10a can be used for securing the medical tubing 12 of a Foley catheter. The medical tubing 12 is commonly a flexible tube for passage of fluid therethrough, and depending on the size of Foley catheter used with the patient, the tubing will have different diameters. The securement device 10a includes channels 16a-c differently sized to accommodate various sizes of Foley catheter tubing. In embodiments of the present invention, the diameters or width of the channels 16a, 16b, and 16c are 4 mm, 5 mm, and 6 mm, respectively. Other channel sizes may also be used, such that the channel sizes may be larger or smaller depending on tubing dimensions or a preferred use or application for the securement device 10a. In embodiments of the present invention, the channel is sized so that the medical fixture 12, e.g., the tubing of a Foley catheter, rests within the channel 16 but is not substantially crimped or otherwise substantially occluded so as to adversely affect or interfere with fluid flow therethrough. However, the channel sizes are also such that lateral (along the width of the base 12), longitudinal (along the length of the base 12), or vertical movement of the medical fixture 12 held within the channel 16 is not permitted or is otherwise substantially inhibited. In alternative embodiments of the present invention, medical fixtures such as medical tubing not affiliated with a Foley catheter may be retained within the channels 16a-c of the securement device 10a.

Referring to FIGS. 2-3, each channel 16 extends along the length of the base 14 from the front end 26 to the rear end 28 and is open along its top and closed along its bottom to include a generally arcuate channel wall 42, a front channel end 44 formed in the front end wall 34 of the base 14, and a rear channel end 46 formed in the rear end wall 36 of the base 14. The arcuate channel wall 42 is generally curved along its width and generally straight or linear along its length, such that the channels 16a-c are generally parallel to each other. In embodiments of the present invention, each channel wall 42 presents a generally semicircular vertical cross section along the base's width, as best illustrated in FIG. 6. This also results in the front and rear channel ends 44,46 being generally semicircular in vertical cross section, as best illustrated in FIGS. 2 and 3. The channel wall 42 may be other arcuate shapes in vertical cross section along the base's width, such as elliptical, oval, or U-shaped.

As noted above, the top of the channel 16 is open. Let the top wall 38 of the base 14 define an imaginary plane 48, as illustrated in broken line on the middle channel 16b in FIG. 3. A height of the channel 16 then extends from a bottom 50 or trough of the channel 16 to the imaginary plane 48 along the top wall 38 of the base 14. Thus, the height of the channel 16 at the front and rear channel ends 44,46 extends from a lowermost point 52 of the respective channel end 44,46 and to the imaginary plane 48.

Referring to FIG. 5, to assist with inhibiting movement of the medical fixture 12 held within each channel 16, the channel wall 42 is vertically raised, relative to the lowermost point 52 of the front and rear channel ends 44,46, along at least a portion of the channel's length, such that the channel 16 presents a concavity 54 or "hump" extending along at least part of the length of an interior of the channel 16. The concavity 54 includes two acclivities 56 or upwardly extending segments and a maximum segment 58 or crest disposed between the acclivities 56 and presenting an uppermost height of the concavity 54. In embodiments of the present invention, the concavity 54 extends along at least approximately 25% the length of the channel, along at least approximately 50% the length of the channel, along at least approximately 75% the length of the channel, or along substantially the entire length of the channel. In alternative embodiments of the present invention, the channel 16 may include two or more concavities 54 (not shown), and the heights of the concavities may be the same or may vary. In even further alternatives of the present invention, the channel 16 may include one or more convexities or depressions (not shown) extending below the lowermost point 52 of the front and rear channel ends 44,46.

In view of the concavity 54, the channel's height is not the same at each point along the length of the channel 16. If one concavity 54 is employed in the channel 16 and is centered along the length of the channel, then the maximum segment 58 of the concavity 54 will be located approximately midway the length of the channel. In such instance, the channel's height is shortest approximately midway along the length of the channel 16 and largest at the front and rear channel ends 44,46. Stated alternatively, a portion of the length of the bottom 50 of the channel wall 42 is raised above a horizontal elevation of the lowermost point 52 of the front and rear channel ends 44,46. In embodiments of the present invention, a height of the concavity 54 from its lowermost point (which would lie in the same plane as the lowermost point 52 of the front and rear channel ends 44,46) to its uppermost point is less than approximately 80% the largest height of the channel (which is at the front and rear channel ends 44,46), is less than approximately 60% the largest height of the channel, or is less than approximately 40% the largest height of the channel. Alternatively stated, a ratio of the largest height of the channel to the height of the concavity 54 is approximately greater than or equal to 1.5:1, approximately greater than or equal to 2:1, approximately greater than or equal to 3:1, or approximately greater than or equal to 4:1. It is to be appreciated that the height of the channel 16 at any point along its length could be varied dependent on the concavities or convexities employed in the channel, and thus, use of the concavity 54 (or convexity, as the case may be) presents a channel height that is not the same along all points of the channel length.

The channel wall 42 can be further reinforced or modified to facilitate inhibition of the medical fixture 12 held in the channel 16 in addition to or in place of the above-described concavity 54. In embodiments of the present invention, the channel wall 42 may include at least one and preferably a plurality of gripping protrusions (not shown) formed in or on the channel wall and extending towards an interior of the channel. Unlike the above-described concavity 54 that projects relatively significantly into the interior of the channel 16, the gripping protrusions are substantially shorter in height (e.g., approximately less than 5-10% the height of the channel) and comprise at least 5, 10, 20, or even 30 protrusions. The protrusions frictionally engage the medical fixture 12 held within the channel 16 to assist in inhibiting movement.

In even further embodiments of the present invention, the channel wall 42 may be formed of or lined with a material (not shown) to frictionally engage the medical fixture 12 held within the channel 16. Exemplary materials include a neoprene or other elastomeric material providing a high coefficient of friction relative to the material of the medical fixture 12. Use of the gripping protrusion and/or friction material may be used in combination with or in place of the concavity 54.

Turning now to FIGS. 2-3 and 6, the strap 18 of the securement device 10a is illustrated and described. The strap 18 is operable to secure the medical fixture 12 in the channel 16 during use of the securement device 10a, as described in more detail below. The flexible strap 18 includes a body 60 and a grasping tab 62. The strap 18 is formed of a thermoplastic elastomer (TPE), SANTOPRENE®, silicon, neoprene, or other suitable material that allows for a relatively small degree of stretching of the body 60 along its width while still maintaining suitable elasticity and rigidity to insure contact with the coupled medical fixture 12 when the strap 18 is coupled to the base 14. In embodiments of the present invention, the strap 18 may include a bacterial or microbial inhibitor either coated on the strap or manufactured into the strap 18 material.

The body 60 of the strap 18 has a width that, when the strap 18 is coupled to the base 14, extends laterally across the width of the base 14 (see FIGS. 2-3). A length of the body 60 of the strap 18 is measured along the longitudinal axis of the base. As illustrated in FIGS. 2-3, the length of the body 60 of the strap 18 is substantially shorter than the length of the base 14, whereas the width of the body 60 of the strap 18 is larger than the width of the base. In embodiments of the present invention, the length of the body 60 of the strap 18 is at least approximately 15%-120% the length of the base, is at least approximately 25%-75% the length of the base, or is at least approximately 40%-60% the length of the base.

The body 60 of the strap 18 includes a top face 64, a bottom face 66 (see FIG. 15), and left and right ends 68,70. Portions of the coupling assembly 20, described below, are provided on the bottom face 66 of the strap 18. The grasping tab 62 of the strap 18 extends from the right end 70 of the body 60 and provides an area that a clinician can grasp and hold to couple the strap 18 with the base 14, as also described in detail below. The grasping tab 62 is preferably integrally formed with the body 60 of the strap 18, although it may be mechanically coupled with the body 60. As illustrated in FIGS. 2-3, the grasping tab 62 may include a ridge 72 or other maneuvering structure to facilitate grasping of the tab 62.

Referring now to FIGS. 2-3 and 6, the coupling assembly 20 for removably coupling the strap 18 to the base 14 is illustrated and described. The coupling assembly 20 comprises left and right tracks 74,76 formed in the left and right side walls 30,32 of the base 14, respectively, and left and right rails 78,80 formed on the bottom face 66 of the strap 18 at the general left and right ends 68,70, respectively, of the strap body 60. The left rail 78 is removably coupled and held within the left track 74, and the right rail 80 is removably coupled and held within the right track 76. As described in detail below, the left and right tracks 74,76 are not shaped the same and have different vertical cross-sectional shapes, and similarly, the left and right rails 78,80 are not shaped the same and have different vertical cross-sectional shapes. In alternative embodiments of the present invention, the left and right rails 78,80 and the left and right tracks 74,76 may, respectively, both be of the same shape. Thus, the left rail 78 would be of the same shape as the right rail 80, and the left track 74 would be of the same shape as the right track 76 (e.g., both tracks would extend horizontally from the base 14 and be generally parallel to the bottom wall of the base, as describe below for the left track).

Figure 14:
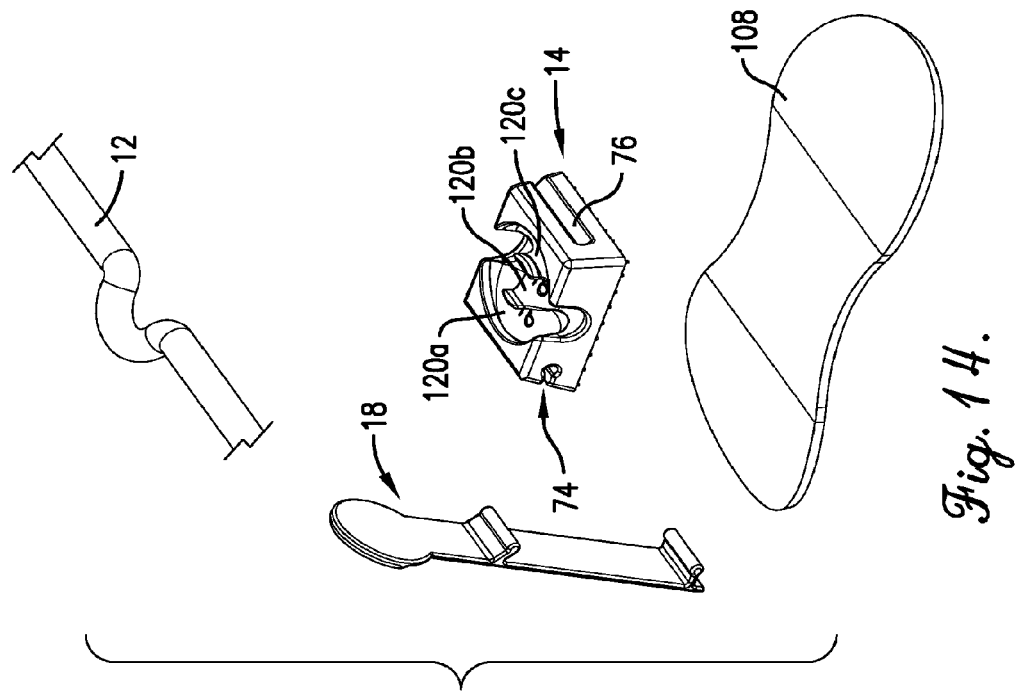
FIG. 14 is another exploded view of the components of the securement device of the second embodiment.
Figure 13:
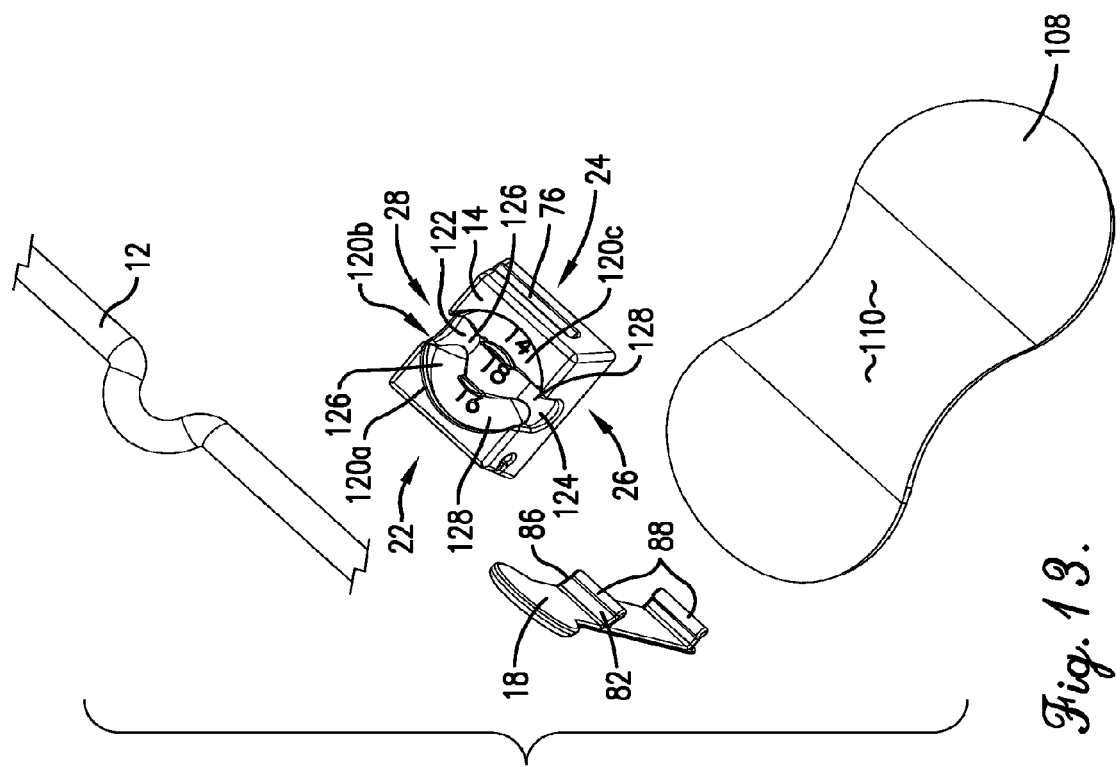
FIG. 13 is an exploded view of components of the securement device of the second embodiment, including the medical tubing, a base, a flexible strap, and an adhesive pad.
Figure 15:
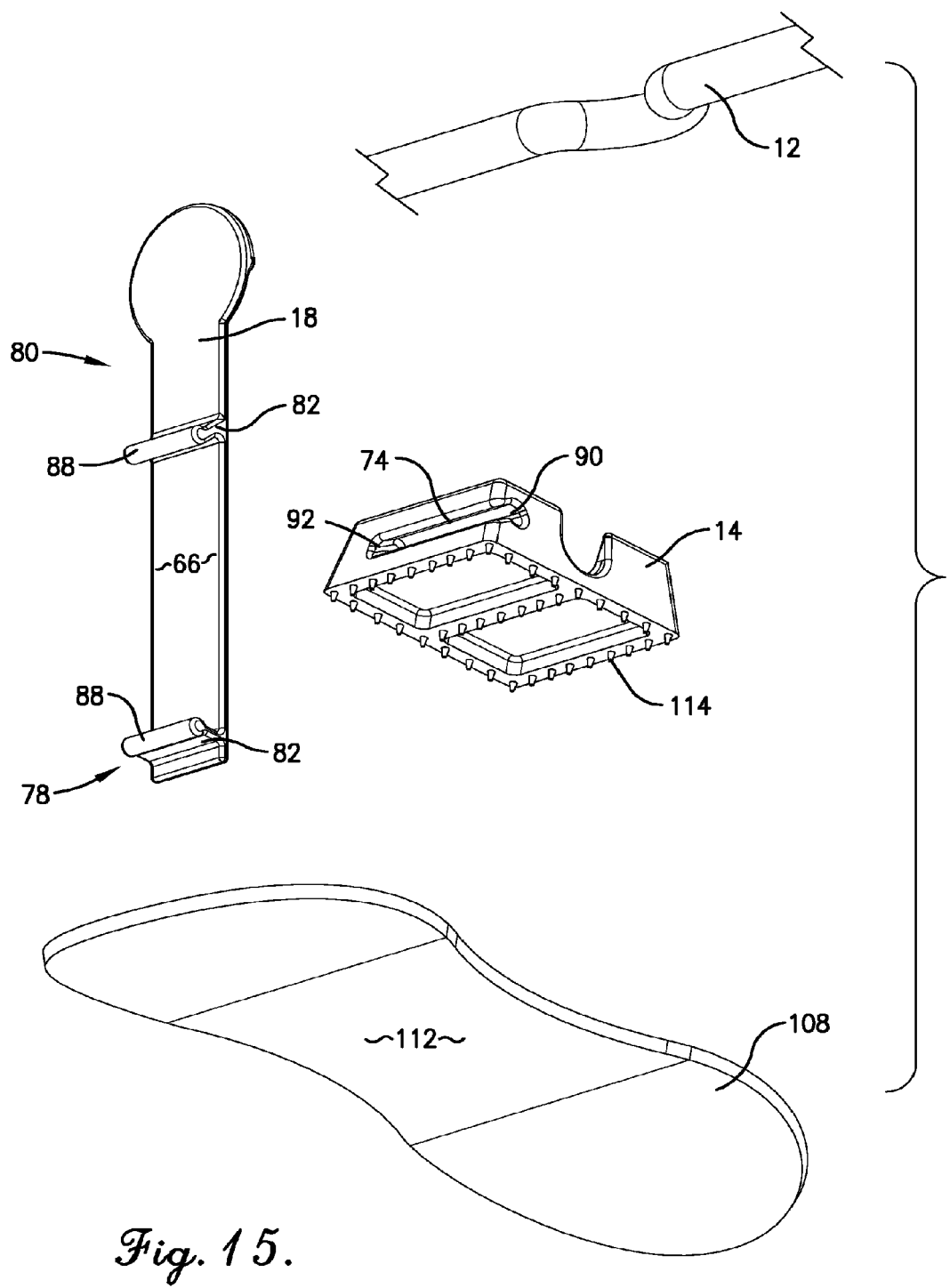
FIG. 15 is yet another exploded view of the components of the securement device of the second embodiment.
Figure 16:
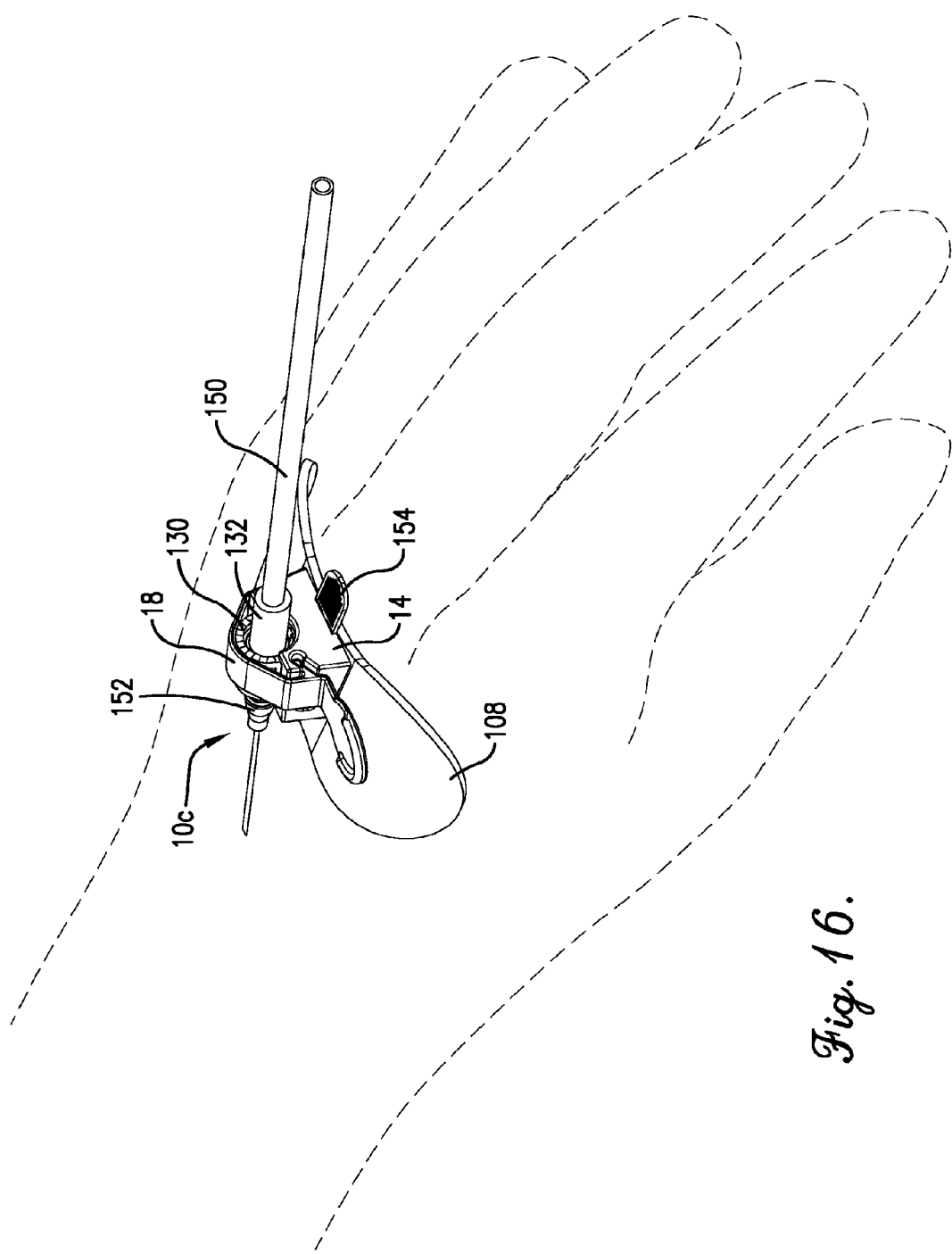
FIG. 16 is an environmental view of a securement device of a third embodiment of the present invention for use with a peripherally inserted central catheter, wherein the securement device is secured to a patient's hand.

As illustrated in FIGS. 6 and 13-15, each of the rails 78,80 formed on the strap 18 has an elongated body 82 integrally formed with and extending from the bottom face 66 of the strap body 60 and longitudinally along the length of the strap 18. (It is noted that FIGS. 13-15 are specific to a second embodiment of the present invention, described below, but that the coupling assembly 20 for both embodiments is substantially similar). An end 86 of the elongated body 82 of the rail 78,80 is integrally formed with or otherwise provided with an elongated bead 88. The elongated rail body 82 is of a generally rectangular shape when viewed from a side (see FIGS. 13-14) and when viewed in vertical cross section (see FIG. 6). In contrast, the elongated bead 88 is of a generally circular shape when viewed on vertical cross section (see FIG. 6). The height of the rails 78,80 (as measured from the bottom face 66 of the strap body 60 to the outermost edge of the bead 88) is approximately 3 mm, the width of the rails (as measured along the lateral axis of the base when the strap is secured to the base) is approximately 1 mm, and the length of the rails (as measured along the longitudinal axis of the base when the strap is secured to the base) is approximately 10 mm. As can be appreciated, the measurements for the rails 78,80 may be modified depending on the size of the strap 18 and/or the base 14. As illustrated in FIG. 13, the length of the rails 78,80 is approximately the same as the length of the strap body 60, although it may be less.

As noted above, the rails 78,80 are preferably integral with the strap body 60. The rails 78,80 are also formed of the same material as the strap 18, such as thermoplastic elastomer ("TPE"). However, unlike the strap body 60, which is flexible and stretchable, the rails 78,80 are molded to be substantially rigid while still having a small degree of compressibility to allow for very small movement of the rails (e.g., less than or equal to approximately 2 mm and more preferably less than or equal to approximately 0.5 mm). As discussed in detail below, this very small degree of compressibility allows the rails 78,80 to more easily interfit with the tracks 74,76 for coupling of the strap 18 to the base 14. Additionally, the elongated body 82 of each rail 78,80 may be bendable about a longitudinal axis to assist in coupling of the strap 18 to the base 14.

Referring now to FIGS. 2-3 and 6, the left and right tracks 74,76 are formed in the respective left and right side walls 30,32 of the base 14. More particularly, the left and right tracks 74,76 are formed through at least a portion of the longitudinal length of the respective side wall 30,32 of the base 14. As illustrated in FIG. 3, the left track 74 formed in the left side wall 30 of the base 14 extends from the front end 26 of the base and towards the rear end 28. However, the left track 74 does not extend through the longitudinal length of the base 14. Thus, the left track 74 at the front end 26 of the base 14 has an open end 90 that is accessible, and the left track 74 at the rear end 28 of the base 14 has a closed end 92 that is inaccessible.

The right track 76 is oriented in the opposite direction as the left rack 74. Referring to FIG. 2, the right track 76 formed in the right side wall 32 of the base 14 extends from the rear end 28 of the base and towards the front end 26. However, the right track 76 does not extend through the longitudinal length of the base 14. Thus, the right track 76 at the rear end 28 of the base 14 has an open end 94 that is accessible, and the right track 76 at the front end 26 of the base 14 has a closed end 96 that is inaccessible. Thus, the tracks 74,76 have open ends 90,94, respectively, that are open and accessible on opposite ends 24,26 of the base 14.

In alternative embodiments of the present invention, the left track 74 may be open and accessible on the rear end 28 of the base 14, and the right track 76 may be open and accessible on the front end 26 of the base 14. In even further alternatives, the left and right tracks 74,76 may be open and accessible on the same end of the base 14. In yet another alternative, the tracks 74,76 may extend the entire longitudinal length of the base 14, such that the tracks 74,76 are open and accessible at both the front end 26 and the rear end 28 of the base 14.

Each track 74,76 has a generally cylindrical interior groove 98 or recess and an exterior bearing 100 or throat. Each of the bearings 100 for the tracks 74,76 includes bottom and top bearing walls 102,104. The bottom and top bearing walls 102,104 of the left track 74 extend substantially horizontally with respect to the horizontal plane of the base 14. In contrast and as best illustrated in FIG. 6, the bottom and top bearing walls 102,104 of the right track 76 are angled upwardly from the right side wall 32 of the base 14 at an approximately 45° above the horizontal plane.

As noted above, the left rail 78 is configured for removably coupling with the left track 74 formed in the left side wall 30 of the base 14, and similarly, the right rail 80 is configured for removably coupling with the right track 76 formed in the right side wall 32 of the base 14. As such, the tracks 74,76 act as sleeves to receive the respective rail 78,80. The left rail 78 is interfit or coupled with the left track 74 by first aligning a rear end of the left rail 78 with the open end 90 of the track 74 and sliding the elongated bead 88 of the rail 78 along and within the groove 98 of the left track 74. Similarly, the right rail 80 is interfit or coupled with the right track 76 by first aligning a front end of the rail 80 with the open end 94 of the right track 76 and sliding the elongated bead 88 of the right rail 80 along and within the groove 98 of the right track 76. For both the left and right rails and tracks, the elongated body 82 of the rail 78,80 bears against the bearing 100 of the track 74,76, while the elongated bead 88 of the rail 78,80 fits within the interior groove 98.

As noted above, the vertical cross-sectional shapes of the respective left and right rails 78,80 and left and rights tracks 76,78 are different. For the left track 74, a diameter of the groove 98 of the track 74 is approximately the same as a diameter of the elongated bead 88 of the left rail 78. Thus, when the left rail 78 is inserted into the left track 76, there are no substantial recesses, grooves, or open areas between an exterior surface of the rail and an interior surface of the track, as best illustrated in FIG. 6. Alternatively, the diameter of the groove 98 of the left track 74 may be slightly less than the diameter of the elongated bead 88 of the left rail 78, and the compressibility of the bead 88 allows for interfitting the left rail 78 within the left track 74. Regardless of the respective diameter sizes of the groove 98 and the elongated bead 88 of the left track/rail 74,78, the elongated body 82 and elongated bead 88 of the left rail 78 is shaped and sized to fit snugly within the left track 74, and the bearing 100 of the left track 74 is shaped to receive the elongated body 82 of the left rail 78.

In contrast, when the right rail 80 is inserted into the right track 76, there is a small volume 106 of the groove 98 of the right track 76 not filled by the elongated bead 88 of the right rail 80. Thus, the diameter of the groove 98 on the right track 76 is slightly larger than the diameter of the elongated bead 88 on the right rail 80. This results in the right rail 80 having a small degree of movement within the right track 76, which facilitates coupling of the right end 70 of the strap body 60 to the base 14.

Referring to FIG. 6, the diameter of the elongated bead 88 on the rails 78,80 is larger than a height between the bottom and top walls 102,104 of the bearing 100 of the tracks 74,76. In embodiments of the present invention, the compressibility of the rails 78,80 is not so large as to allow the clinician or another user to laterally push the bead 88 between the bearing walls 102,104 and into the groove 98 of the respective track 76,78. Thus, the clinician must slide the rail into the track, as described above. Due to the slightly different diameter sizes of the groove 98 and bead 88 and the coefficient of friction between the TPE material of the strap 18 and the plastic material of the base 14, the rail is held within the track. However, in alternative embodiments of the present invention, the rails can be pushed or snap-fit laterally into the tracks along a plane generally perpendicular to the longitudinal axis of the base 14. In such an embodiment, the elongated bead 88 on each rail 78,80 is sufficiently flexible and deformable to overcome the smaller height between the lower and upper walls 102,104 of the bearing 100.

The reverse or opposite orientation of the respective open ends 90,94 of the left and right tracks 74,76 further assists in coupling the strap 18 to the base 14. During use of the securement device 10a by the patient, each rail may possibly longitudinally move within its respective track to some degree. However, the opposite orientation of the open ends 90,04 of the tracks 74,76 requires a greater degree of a twisting motion to achieve complete separation of a rail from its track. As noted above, the rails are firmly held within the track via the mating arrangement of the rail and track and the friction fit; thus, for the rails and tracks to separate requires substantial movement of the strap 18 relative to the base 14.

The securement device 10a may also include an adhesive pad 108 to which the base 14 is secured. The adhesive pad 108 is preferably sized to receive the entirety of the base bottom wall 40 and to include additional area for secure lodging of the pad 108 on the patient's skin. The adhesive pad 108 may include a top side 110 to which the bottom wall 40 of the base 14 is permanently secured and a bottom side 112 having an adhesive surface for removably coupling with the patient's skin (see FIGS. 13 and 15). The adhesive surface on the bottom side 112 may include a removable covering (not shown) kiss-cut to the shape of the adhesive pad 108. Prior to placement of the securement device 10a against the patient's skin, the covering is removed to expose the adhesive surface.

The bottom wall 40 of the base 14 may be permanently secured to the bottom side 112 of the adhesive pad 108 via known techniques. In embodiments of the present invention, the bottom wall 40 of the base 14 is provided with a plurality of spikes 114 (see FIGS. 6 and 15). Upon heating of the spikes 114 when the pad 108 is adjacent the bottom wall 40 of the base 14, the spike tips expand into the top side 110 to undertake a mushroom shape that interconnects the base 14 with the pad 108.

Operation and use of the securement device 10a will now be described. In operation, the left rail 78 is first coupled with the left track 74 as described above, if not already coupled upon opening of the securement device 10a package. In preferred use, the left rail 78 is already coupled with the left track 74 when delivered for use by the clinician. The clinician then lays the medical fixture 12 into the appropriately-sized channel 16 for the medical fixture's diameter. As noted above, in embodiments of the present invention and during use of the securement device 10a, only one of the plurality of channels 16a-c is used at a single time. The clinician then grips the grasping tab 62 of the strap 18 and lays the strap body 60 over the top wall 38 of the base 14 and the associated medical fixture 12 held within the base 14. The clinician couples the right rail 80 with the right track 76, as described above. The clinician may need to slightly stretch the strap 18 so as to provide enough clearance to perform the coupling of the right rail 80 with the right track 76. To assist in the coupling of the rails 78,80 with the tracks 74,76, the clinician can obtain stability and leverage by pressing and perhaps pulling on the grasping tab 62. Finally, the clinician removes the covering on the adhesive pad's bottom side 112 and applies the adhesive pad 108 to the patient's skin, thereby securing the medical fixture 12 to the patient's skin. In alternative steps, the clinician may apply the adhesive pad 108 to the patient's skin and then secure the medical fixture 12 in the securement device 10a.

Referring to FIGS. 5-6, during securement of the medical fixture 12 in the securement device 10a, the medical fixture 12 is preferably not occluded or crimped at all or in an amount that does not adversely affect fluid flow therethrough. Although the strap 18 is slightly stretched during coupling of the strap 18 to the base 14, the respective coupling assembly 20 parts of the strap 18 and base 14 are sized to allow the strap 18 to lie over the top wall 38 of the base 14 without applying significant occluding pressure to the medical fixture 12 held in the channel 16 of the base 14. However, the TPE material of the strap assists in securing the medical fixture 12 within the base by frictionally engaging the medical fixture 12 where the fixture and strap are in contact, as illustrated in FIG. 6.

As noted above, the concavity 54 in the channel 16 of the base 14 also assists in retaining the medical fixture 14 within the base 14. As best illustrated in FIG. 5, the concavity 54 forces the medical fixture 12 to undertake a change in orientation or elevation along a portion of its longitudinal length, such that the medical fixture 12 presents an acclivity 116 and a declivity 118 as the medical fixture 12 lies longitudinally within the channel and extends from the rear end 28 of the base 14 and to the front end 26 of the base 14. The change in elevation of the medical fixture 12 reduces the ease by which the medical fixture 12 can be pulled through the channel 16, even when the strap is overlaying the fixture 12.

Second Embodiment of a Securement Device for a Foley Catheter

Referring now to the embodiment disclosed in FIGS. 7-15, a securement device 10b for a medical fixture 12 comprising a Foley catheter is illustrated. In alternative embodiments of the present invention, medical fixtures such as medical tubing not affiliated with a Foley catheter may be retained within the channels of the securement device 10b. As noted above, structural features of device 10b that are substantially similar to the structural features of device 10a will be provided with like reference numerals.

The securement device 10b of the second embodiment is similar to the securement device 10a of the first embodiment in many respects, and both are for preferable use with a Foley catheter or for medical tubing. However, the securement device 10b is primarily different from the device 10a due to the arrangement and shape of channels 120a-c. As best illustrated in FIGS. 7, 13, and 14, instead of three generally straight and parallel channels 16a-c, as provided for in securement device 10a, the channels 120a-c of device 10b intersect along a portion of their respective lengths. At least one and preferably two of the channels, namely 120a and 120c (i.e., the two outer channels), are curved or otherwise arcuate along their longitudinal length. More or less channels could be provided. The curved, intersecting channels 120a-c of the securement device 10b provide an even increased friction coefficient for improved securement of the medical fixture 12.

Similar to the first embodiment, the three channels 120a-c are formed in the top wall 38 of the base 14 and have different diameters to accommodate various diameters of medical tubing 12 for use with a Foley catheter. As illustrated in FIG. 13. the smallest diameter channel 120c is on the right side 24 of the base 14, the second largest diameter channel 120a is on the left side 22 of the base 14, and the largest diameter channel 120b lies approximately midway along a lateral width of the base 14 (the diameter size indicator, e.g., 14, 16, 18, shown on the channels is for reference only and may or may not be provided on the securement device 10b). The channels 120a-c could also be arranged differently, such that the smallest diameter channel was in the middle, the largest diameter channel was on the on the left side 22 of the base, and the second largest diameter channel was on the right side 24 of the base. Reference to channel 120a refers to the channel on the left side 22 of the base 14, regardless of the size of the channel; similarly, channel 120b is the middle channel, and channel 120c is the channel on the right side 24 of the base 14.

The left channel 120a and the right channel 120c are generally semicircular, or, at the least, arcuate, in plan view and along their longitudinal length. A portion of the longitudinal length of each of the channels 120a-c intersects, such that the three separated channels merge into one channel at the front and rear ends 26,28 of the base 14. This, in return, presents a single rear channel end 122 and a single front channel end 124.

In more detail, each channel 120a-c includes a rear end segment 126 at the general rear end 28 of the base 14 and a front end segment 128 at the general front end 26 of the base 14. Because the front and rear end segments 126,128 of the left and right channels 120a,120c curve inwardly towards the middle channel 120b and intersect the respective front and rear end segments 126,128 of the middle channel 120b, the front and rear end segments 126,128 of each channel are the same structure. Stated alternatively, the front and rear end segments 126,128 of each of the channels 120a-c generally comprise the same respective front and rear longitudinal segment length. This is a result of the channel ends merging or otherwise intersecting to present the single rear channel end 122 and the single front channel end 124. The merging of the channels 120a-c also creates a single horizontal channel entry and a single horizontal channel exit in the base for locating the medical fixture longitudinally in the base. In operation and as illustrated in FIG. 7, only one channel 120a-c can be used at a time, such that the securement device 10b is operable to receive only one medical fixture 12 at a single time.

Figure 12:
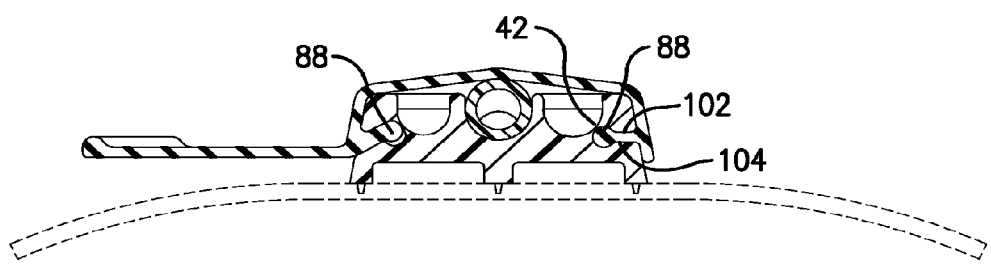
FIG. 12 is a vertical cross-sectional view through line 12-12 of FIG. 11.

Referring to FIG. 12, each channel 120a-c includes a channel wall 42 that is substantially arcuate in vertical cross section, similar to the channels 16a-c of the securement device 10a. In more detail, each 120a-c is generally U-shaped in vertical cross-section, although the channels 120a-c could be semicircular, oval elliptical, and other arcuate shapes.

Figure 11:
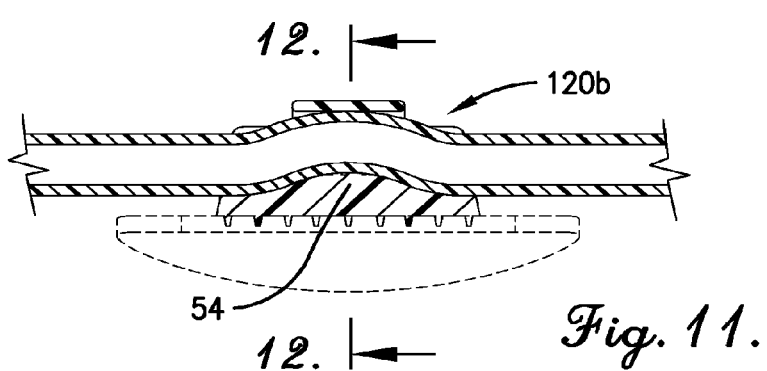
FIG. 11 is a vertical cross-sectional view through line 11-11 of FIG. 10.

Referring to FIG. 11, the middle channel 120b includes the concavity 54, similar to the concavity of the channels 16a-c in the securement device 10a. A concavity is not required for the two outer channels 120a,120c due to the curved shape undertaken by the medical fixture 12 when placed in said channels, as best illustrated in FIGS. 7 and 14. The curved shape along the medical fixture's longitudinal length assists in securing the medical fixture 12 within the base 14 of the securement device 10b and inhibiting or restricting longitudinal movement of the fixture 12 within the device 10b.

In alternative embodiments of the present invention, the two outer channels 120a,120c may include inwardly tapered or angled channel wall faces (not shown). In more detail, for each channel wall 42, a portion of the outermost segment of the channel wall (i.e., the segment of the channel wall closest to the respective base 14 side), is tapered. The entire outermost segment of the channel wall 42 need not be angled. However, an inward taper of a portion of the outermost segment may facilitate inhibiting longitudinal movement of the respective channels 120a,120c. The angle of inward taper may be approximately 10°-80° relative to a vertical axis, approximately 20°-70° relative to a vertical axis, or approximately 30°-60° relative to a vertical axis.

Other than the channels 120a-c formed in the base 14, the base 14 is substantially similar to the base 14 of the first embodiment. Similarly, the flexible strap 18, coupling assembly 20, and adhesive pad 108 of the securement device 10b of the second embodiment are substantially similar to the like elements of the securement device 10a of the first embodiment and will not otherwise be described herein.

Third Embodiment of a Securement Device for a Peripheral Catheter

Referring now to the embodiment disclosed in FIGS. 16-22, a securement device 10c for a medical fixture 12 comprising a peripheral catheter is illustrated. As noted above, structural features of devices 10a,10b that are substantially similar to the structural features of device 10c will be provided with like reference numerals.

The securement device 10c of the third embodiment is similar to the securement devices 10a,10b of the first embodiment in some respects, including, notably, the strap 18 and coupling assembly 20. However, the third embodiment is a securement device for a spin nut 130 conventionally coupled with a catheter hub 132. Thus, the securement device 10c is primarily different from the devices 10a,10b in the arrangement and shape of a channel 134. There are structural differences in the base 14 and some structural differences in the coupling assembly 20 that will be further described herein.

Figure 17:
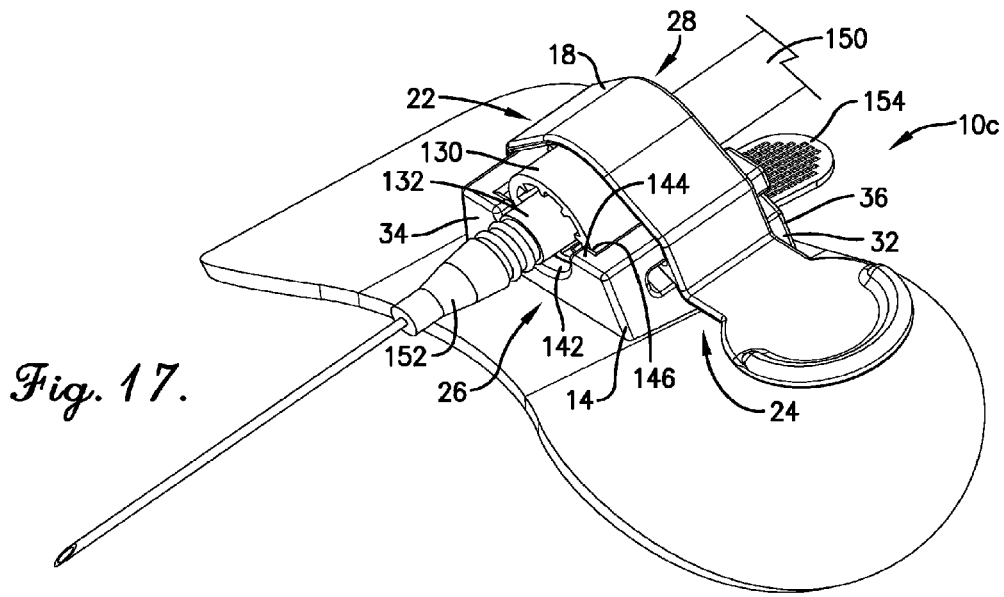
FIG. 17 is a front isometric view of the securement device of FIG. 16.
Figure 18:
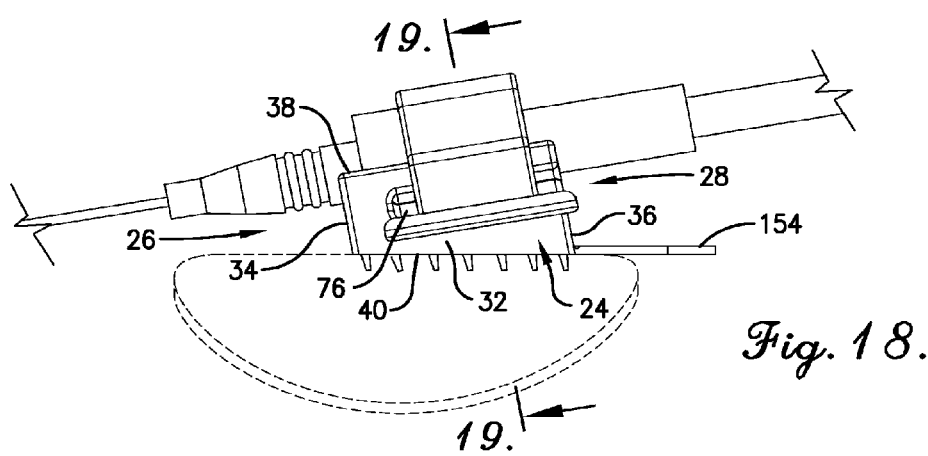
FIG. 18 is a right side view of the securement device of FIG. 17 and illustrating an adhesive pad in phantom.
Figure 19:
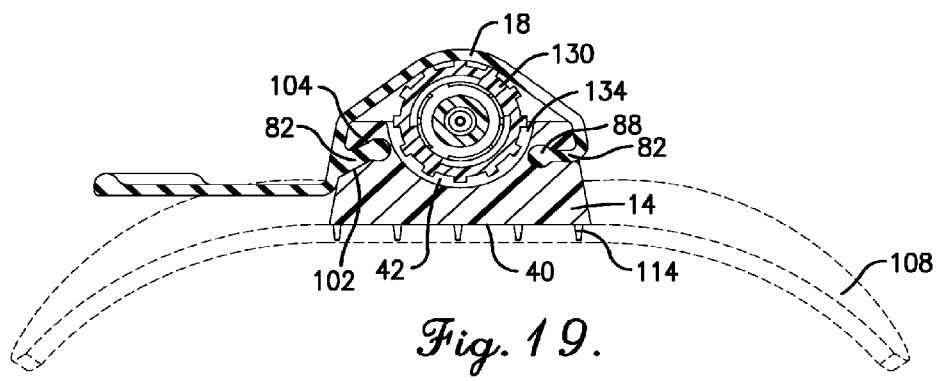
FIG. 19 is a vertical cross-sectional view through line 19-19 of FIG. 18.
Figure 21:
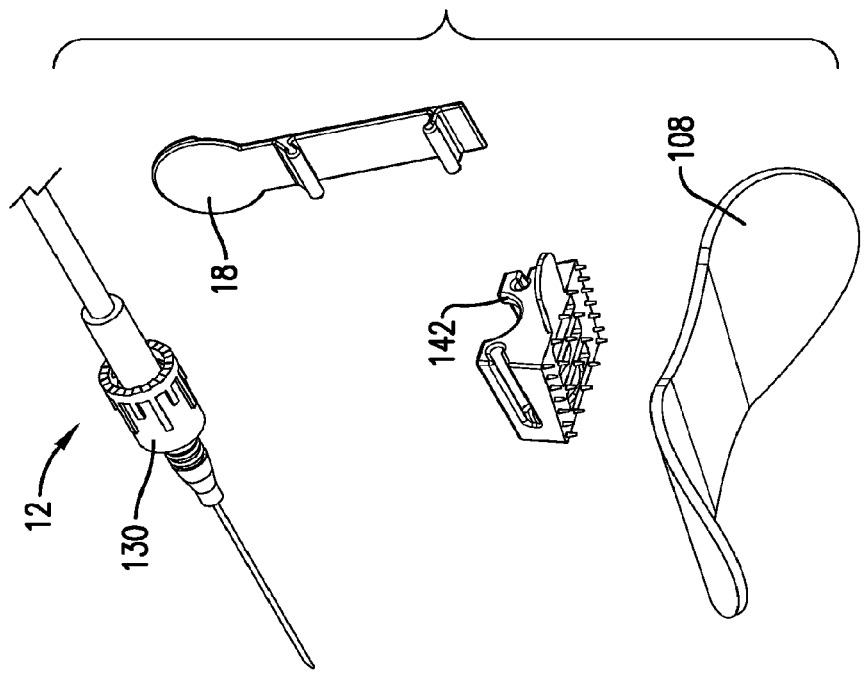
FIG. 21 is another exploded view of the components of the securement device of the third embodiment.
Figure 20:
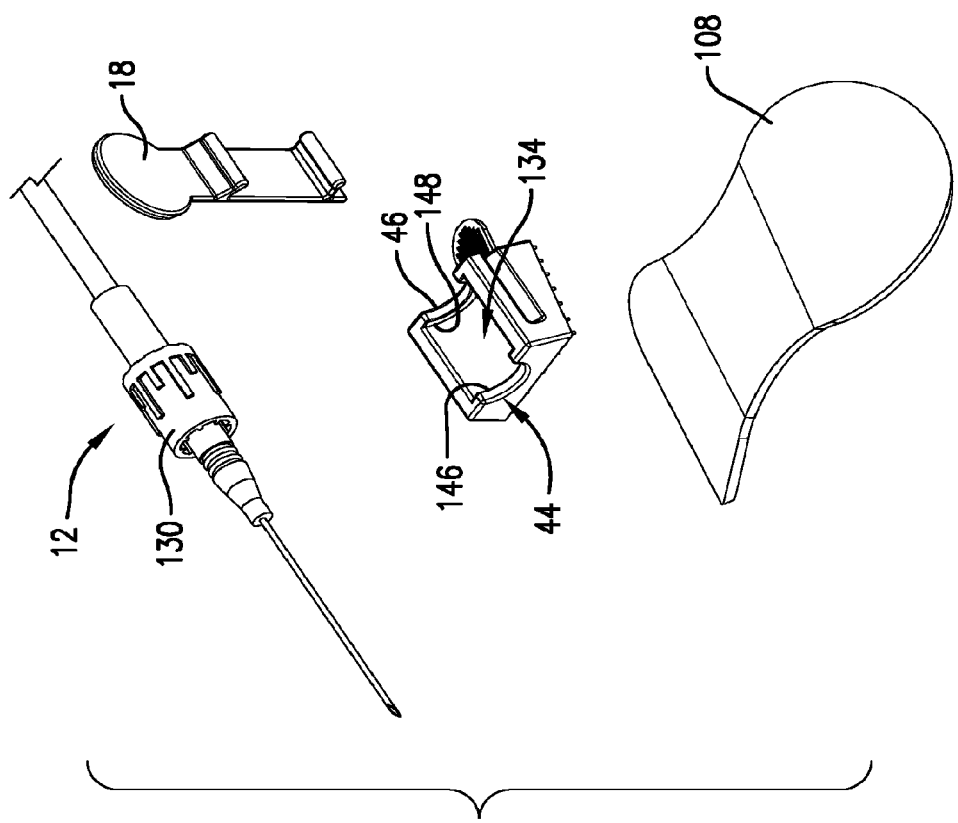
FIG. 20 is an exploded view of the components of the securement device of the third embodiment, including the medical fixture, a base, a flexible strap, and an adhesive pad.

Referring to FIGS. 17-19, the base 14 includes left and right sides 22,24, front and rear ends 26,28, left and right side walls 30,32, front and rear end walls 34,36, top wall 38, and bottom wall 40. The base 14 is angled downwardly from the rear end 26 and to the front end 28, as best illustrated in FIG. 18. The base includes channel 134 formed in the top wall 38, as best illustrated in FIG. 20. The channel 134 includes an arcuate channel wall 42, that in embodiments of the present invention, is generally semicircular, as best illustrated in FIGS. 19 and 20. Other arcuate channel wall 42 shapes may be used, such as U-shaped, elliptical, or oval. Unlike the first embodiment and device 10a, the channel 134 does not have the same diameter along the entirety of its longitudinal length. Instead, for device 10c, the channel 134 presents two diameters, namely a first diameter 136 along a primary channel length 138 that holds the spin nut 130, and a second, smaller diameter 140 at the front and rear end walls 34,36 of the base 14, as best illustrated in FIGS. 17 and 22.

For the securement device 10c, the base 14 is sized differently than for the securement devices 10a,b of the first and second embodiments. In particular, the width of the base 14 is approximately 5-35 mm, approximately 10-30 mm, or approximately 15-25 mm. The length of the base 14 is approximately 5-30 mm, approximately 10-25 mm, or approximately 15-20 mm. A height of the base 14 from the bottom wall 40 to the top wall 38 and at the rear end of the base is approximately 2-20 mm, approximately 5-15 mm, or approximately 8-12 mm. A height of the base 14 at the front end of the base is approximately 2-12 mm, approximately 4-10 mm, or approximately 6-8 mm.

In more detail, the front and rear end walls 34,36 of the base 14 each includes a generally arcuate, and in embodiments of the present invention, a semicircular cut-out 142 (in vertical cross section). A rearmost cut-out 142 forms the rear channel end 46, and a frontmost cut-out 142 forms the front channel end 44. The cut-out 142 may be other arcuate shapes or may even include right angles, such as a generally rectangular shape in vertical cross section. A secondary channel length 144 comprises the small longitudinal segments of the combined lengths of each of the cut-outs 142. As illustrated in FIG. 22, the primary channel length 138 is significantly greater than the secondary channel length 144, such that the secondary channel length 144 is less than approximately 25% the primary channel length or is less than approximately 15% the primary channel length. Thus, the overall channel length comprises the length of the rearmost cut-out, the primary channel length in which the spin nut lies, and the frontmost cut-out. The diameter of the front and rear end channel ends 44,46 is the second diameter, which, as noted above, is less than the first diameter of the primary channel length 138.

Figure 22:
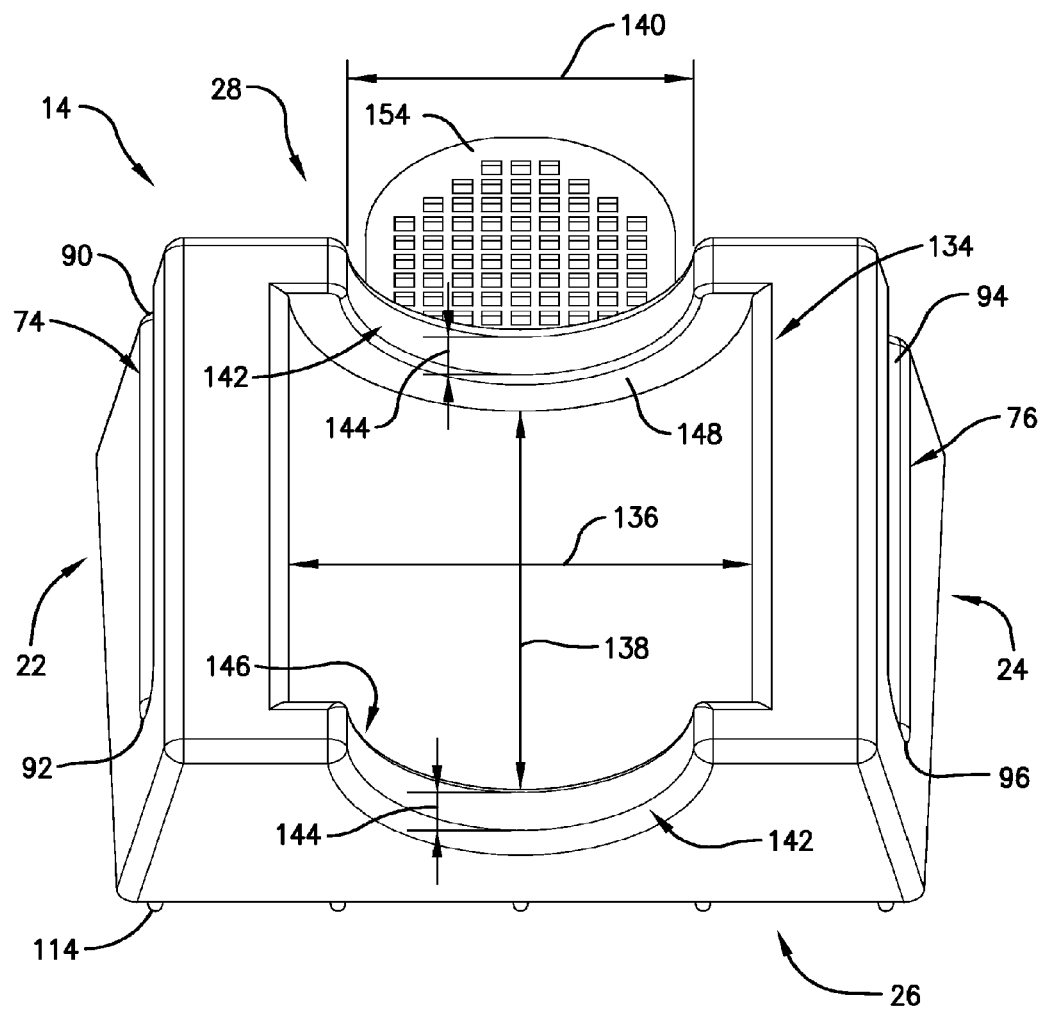
FIG. 22 is an isometric view of the base of the securement device of the third embodiment.

The cut-outs 142 having the second, smaller diameter create front and rear interior channel faces 146,148, as best illustrated in FIGS. 20 and 22. The spin nut 130, when placed in the primary channel length 138, abuts against the front and rear end interior channel faces 146,148 to thereby partially secure the spin nut 130 in the securement device 10c and to specifically inhibit longitudinal movement of the spin nut 30 relative to the base 14. Thus, the interior channel faces 146,148 and the primary channel length 138 together form a receiving area for a generally bottom half of the spin nut 130. The second, smaller diameter 140 allows passage of the medical tubing 150 to which the spin nut 130 is affixed from the rear end 28 of the base 14 and further, passage of the luer 152, to which the spin nut 130 is also affixed, from the front end 26 of the base 14, as illustrated in FIG. 17.

As noted above, the base 14 is angled downwardly from the rear end 28 to the front end 26 of the base 14, such that a height of the rear end wall 36 of the base 14 is larger than a height of the front end wall 34 of the base 14. This provides a medically preferred incidental angle of the luer 152 into the patient's skin.

In alternative embodiments of the present invention, the base 14 does not include the rear end wall 36. As such, the securement device 10c would also not include the rearmost cut-out 142 and the rear end interior channel face 148. However, even without the rear end wall 36, the spin nut or other medical fixture 12 can be securely held within the channel 134. Inclusion of the rear end wall 36 may also be dependent on the particular type of medical fixture 12 to be retained.

In embodiments of the present invention, the primary channel length 138 may be provided with gripping protrusions (not shown), as described for the securement device 10a. Either alone or in combination with the gripping protrusions, the primary channel length 138 may also be formed of or lined with a material (not shown) to frictionally engage the medical fixture 12 held within the channel 134, as also described above for securement device 10a.

The strap 18 and coupling assembly 20 of the securement device 10c is substantially similar to the like elements for device 10a, with the primary difference being that the right rail 80 interfits with the right track 76, such that there are no substantial recesses, grooves, or open areas between an exterior surface of the rail and an interior surface of the track, as best illustrated in FIG. 19. Similar to the other described embodiments, the strap 18 is coupled with the base 14, such that the strap 18 overlays the lateral width of the base 14. As best illustrated in FIG. 17, the length of the strap for device 10c is at least approximately 25-120% the length of the base or approximately 40%-70% the length of the base.

The base 14 may also include a secondary hold-down tab 154, as illustrated in FIG. 17, to assist in placement and securement of the device 10c on the patient's skin.

Although the invention has been described with reference to the embodiments illustrated in the attached drawing figures, it is noted that equivalents may be employed and substitutions made herein without departing from the scope of the invention as recited in the claims. For example, the strap 18 may be color-coded to identify it as an intravenous device, may include identifying indicia, or may have an annotation face for providing other identifying information so as to communicate information to a clinician or patient using the securement device 10a-c, such as the date the securement device 10a-c was placed on the patient. Alternatively, the strap 18 may include a barcode, a QR code, an RFID, or other unique mechanical or electronic identifier. In even further embodiments, the base 14 and the strap 18 may be color-coded or provided with identifying indicia to inform the clinician or patient on use of the securement device 10.

Having thus described various embodiments of the invention, what is claimed as new and desired to be protected by Letters Patent includes the following:

1. A securement device for a medical fixture comprising:
    a base having a first end portion and a second end portion and a channel for receipt of a medical fixture therethrough;
    a flexible strap for securing the medical fixture in the channel during use of the securement device, the flexible strap having a body; and
    a coupling assembly for removably coupling the flexible strap to the base, said coupling assembly including—
        a first track formed at the first end portion of the base,
        a second track formed at the second end portion of the base, and
        first and second rails formed on an underside of the body of the flexible strap,
        wherein said first rail is removably coupled and held within the first track, and said second rail is removably coupled and held within the second track,
        wherein each of the first and second tracks extends longitudinally through the respective first and second end portions of the base but does not extend through an entire longitudinal length of the respective first and second end portions of the base, such that each of the first and second tracks has a closed end and an open end.

2. The securement device of claim 1, wherein the channel is curved along a generally horizontal plane, such that the medical fixture located in the channel is curved to prevent movement of the medical fixture relative to the base.

3. The securement device of claim 1,
    wherein the first track is oriented in a first direction relative to the longitudinal length of the first end of the base,
    wherein the second track is oriented in a second direction relative to the longitudinal length of the second end of the base,
    wherein the first direction is opposite the second direction.

4. The securement device of claim 1,
    wherein the base further includes a bottom wall, and
    wherein the securement device further includes an adhesive pad presenting a top side to which the bottom wall of the base is secured and a bottom side having an adhesive surface for removably coupling with a patient's skin.

5. The securement device of claim 1, wherein each of the first and second rails formed on the strap has an elongated body extending from the underside of the strap.

6. The securement device of claim 5,
    wherein the respective elongated bodies of each of the first and second rails formed on the strap has an elongated bead extending from an end of said respective elongated body, and
    wherein each of the first and second tracks formed in the base has an interior groove for receipt of the elongated bead of the rail and an exterior bearing for receipt of the elongated body of the rail.

7. The securement device of claim 1, wherein the channel has a concavity formed along at least a portion of a length of the channel.

8. The securement device of claim 7, wherein securement of the medical fixture in the channel causes the medical fixture to present an acclivity and a declivity along a vertical axis of the channel.

9. The securement device of claim 7,
    wherein the channel further includes a bottom wall, and
    wherein the concavity extends upwardly from the bottom wall of the channel along a vertical axis of the channel.

10. The securement device of claim 9, wherein the concavity extends along at least approximately 50% the length of the channel.

11. The securement device of claim 9,
    wherein the concavity is a first concavity, and
    wherein the securement device further includes a second concavity formed in the channel along said at least a portion of the length of the channel.

12. The securement device of claim 9, wherein a ratio of a largest height of the channel to a height of the channel's concavity is approximately greater than or equal to 2:1.

13. A method of securing a medical fixture comprising the steps of:
    providing a securement device including—
        a base having a first end portion and a second end portion, a bottom wall, and a channel for receipt of a medical fixture therethrough, an adhesive pad presenting a top side to which the bottom wall of the base is secured and a bottom side having an adhesive surface for removably coupling with a patient's skin,
a flexible strap for securing the medical fixture in the channel during use of the securement device, the flexible strap having a body, and
a coupling assembly for removably coupling the flexible strap to the base, said coupling assembly including—
a first track formed at the first end portion of the base,
a second track formed at the second end portion of the base, and
first and second rails formed on an underside of the body of the flexible strap, wherein said first rail is configured to be removably coupled and held within the first track, and said second rail is configured to be removably coupled and held within the second track,
wherein each of the first and second tracks extends longitudinally through the respective first and second end portions of the base but does not extend through an entire longitudinal length of the respective first and second end portions of the base, such that each of the first and second tracks has a closed end and an open end;
instructing a user to couple the first rail with the first track, if said first rail is not provided to the user already coupled with said first track;
instructing the user to secure the base to the adhesive pad to the patient's skin;
instructing the user to place the medical fixture within the channel of the base; and
instructing the user to pull the strap over the base, including over at least a portion of the medical fixture located in the channel, and couple the second rail within the second track.

14. The method of claim 13, wherein the channel is curved along a generally horizontal plane, such that the medical fixture placed in the channel is curved to prevent movement of the medical fixture relative to the base.

15. The method of claim 13,
wherein the first track is oriented in a first direction relative to the longitudinal length of the first end of the base,
wherein the second track is oriented in a second direction relative to the longitudinal length of the second end of the base,
wherein the first direction is opposite the second direction.

16. The method of claim 13, wherein each of the first and second rails formed on the strap has an elongated body extending from the underside of the strap.

17. The method of claim 16,
wherein the respective elongated bodies of each of the first and second rails formed on the strap has an elongated bead extending from an end of said respective elongated body, and
wherein each of the first and second tracks formed in the base has an interior groove for receipt of the elongated bead of the rail and an exterior bearing for receipt of the elongated body of the rail.

18. The method of claim 13, wherein the channel has a concavity formed along at least a portion of a length of the channel.

19. The method of claim 18, wherein upon the medical fixture being placed within the channel of the base, the medical fixture presents an acclivity and a declivity along a vertical axis of the channel.

20. The method of claim 18,
wherein the channel further includes a bottom wall, and
wherein the concavity extends upwardly from the bottom wall of the channel along a vertical axis of the channel.

* * * * *